United States Patent
Rahman et al.

(10) Patent No.: US 7,011,520 B2
(45) Date of Patent: Mar. 14, 2006

(54) TWO PART ULTRASONIC SWIVEL INSERT, WITH ONE PART ROTATABLE RELATIVE TO THE OTHER

(75) Inventors: Anisur Mithu Rahman, Gurnee, IL (US); Shu Chen, Buffalo Grove, IL (US); Patricia H. Parker, Midlothian, IL (US)

(73) Assignee: Hu-Friedy Mfg. Co., Inc., Chicago, IL (US)

( * ) Notice: Subject to any disclaimer, the term of this patent is extended or adjusted under 35 U.S.C. 154(b) by 0 days.

(21) Appl. No.: 10/346,746

(22) Filed: Jan. 17, 2003

(65) Prior Publication Data

US 2003/0108844 A1    Jun. 12, 2003

Related U.S. Application Data

(62) Division of application No. 09/917,101, filed on Jul. 27, 2001, now Pat. No. 6,716,028.

(60) Provisional application No. 60/223,447, filed on Aug. 4, 2000, provisional application No. 60/270,687, filed on Feb. 22, 2001.

(51) Int. Cl.
*A61C 1/07*    (2006.01)
(52) U.S. Cl. ........................................ 433/86
(58) Field of Classification Search ............... 433/119, 433/118, 86, 81, 102
See application file for complete search history.

(56) References Cited

U.S. PATENT DOCUMENTS

| | | |
|---|---|---|
| 2,442,033 A | 5/1948 | Brantly et al. |
| 2,705,838 A | 4/1955 | Blair |
| 2,874,470 A | 2/1959 | Richards |
| RE25,033 E | 8/1961 | Balamuth et al. |
| 3,058,218 A | 10/1962 | Kleesattel et al. |
| 3,075,288 A | 1/1963 | Balamuth et al. |
| 3,076,904 A | 2/1963 | Kleesattel et al. |
| 3,124,878 A | 3/1964 | Bodine, Jr. et al. |
| 3,213,537 A | 10/1965 | Balamuth et al. |
| 3,256,604 A | 6/1966 | Borden |
| 3,368,280 A | 2/1968 | Friedman et al. |
| 3,375,583 A | 4/1968 | Blank et al. |
| 3,488,851 A | 1/1970 | Haydu |
| 3,518,766 A | 7/1970 | Burt |
| 3,522,801 A | 8/1970 | Robinson |
| 3,526,036 A | 9/1970 | Goof |
| 3,589,012 A | 6/1971 | Richman |
| 3,589,363 A | 6/1971 | Banko |
| 3,593,425 A | 7/1971 | Robinson |

(Continued)

FOREIGN PATENT DOCUMENTS

DE    609 508/10    5/1956

(Continued)

OTHER PUBLICATIONS

Product Specification Brochure for Midwest RDH Hygienist Handpieces, copyright 1996, 4 pages.

(Continued)

*Primary Examiner*—Melba N. Bumgarner
(74) *Attorney, Agent, or Firm*—Welsh & Katz, Ltd.

(57) ABSTRACT

An ultrasonic insert carries a rotary bearing adjacent to the transducer. The bearing slidably engages an ultrasonic handpiece. When seated in the handpiece, the insert is substantially decoupled, on a rotary axis, from the handpiece. A rotary force need only be applied to the insert to rotate it in the handpiece. Alternately, an adaptor can be inserted into the handpiece. The adaptor slidably receives a conventional ultrasonic insert. The conventional insert can be easily rotated with a force applied only thereto, relative to the handpiece.

34 Claims, 15 Drawing Sheets

U.S. PATENT DOCUMENTS

| | | |
|---|---|---|
| 3,636,947 A | 1/1972 | Balamuth |
| 3,645,255 A | 2/1972 | Robinson |
| 3,654,502 A | 4/1972 | Carmona et al. |
| 3,703,037 A | 11/1972 | Robinson |
| 3,763,411 A * | 10/1973 | Goof .......................... 318/118 |
| 3,778,903 A | 12/1973 | Gardella et al. |
| 3,805,787 A | 4/1974 | Banko |
| 3,809,977 A | 5/1974 | Balamuth et al. |
| 3,811,190 A | 5/1974 | Sertich |
| 3,823,477 A | 7/1974 | Hedrick |
| 3,886,560 A | 5/1975 | Mortensen et al. |
| 3,930,173 A | 12/1975 | Banko |
| 3,942,392 A | 3/1976 | Page, Jr. et al. |
| 3,986,263 A | 10/1976 | Borgelt et al. |
| 4,038,571 A | 7/1977 | Hellenkamp |
| 4,040,311 A | 8/1977 | Page, Jr. et al. |
| 4,051,337 A | 9/1977 | Warrin |
| 4,080,737 A | 3/1978 | Fleer |
| RE29,687 E | 7/1978 | Sertich |
| 4,110,908 A | 9/1978 | Cranston |
| 4,168,447 A | 9/1979 | Bussiere et al. |
| 4,169,984 A | 10/1979 | Parisi |
| 4,177,564 A | 12/1979 | Flatland |
| 4,213,243 A | 7/1980 | Flatland |
| 4,249,901 A | 2/1981 | Wieser |
| RE30,536 E | 3/1981 | Perdreaux, Jr. |
| 4,260,380 A | 4/1981 | Nash |
| 4,260,382 A | 4/1981 | Thomson |
| 4,281,987 A | 8/1981 | Kleesattel |
| 4,283,174 A | 8/1981 | Sertich |
| 4,283,175 A | 8/1981 | Nash |
| 4,303,392 A | 12/1981 | Rollofson |
| 4,303,393 A | 12/1981 | Gentry |
| 4,315,742 A | 2/1982 | Nash et al. |
| 4,330,274 A | 5/1982 | Friedman et al. |
| 4,332,558 A | 6/1982 | Lustig |
| 4,370,131 A | 1/1983 | Banko |
| D269,122 S | 5/1983 | Seeley |
| 4,406,284 A | 9/1983 | Banko |
| 4,417,578 A | 11/1983 | Banko |
| 4,431,412 A | 2/1984 | Lares et al. |
| RE31,537 E | 3/1984 | Flatland |
| 4,484,892 A | 11/1984 | Pernot et al. |
| 4,492,574 A | 1/1985 | Warrin et al. |
| 4,501,555 A | 2/1985 | Ditchburn |
| 4,501,558 A | 2/1985 | Maliga |
| 4,521,189 A | 6/1985 | Lares et al. |
| 4,534,734 A | 8/1985 | Lares |
| 4,553,938 A | 11/1985 | Olsen |
| 4,578,033 A | 3/1986 | Mossle et al. |
| 4,589,847 A | 5/1986 | Loge et al. |
| 4,608,622 A | 8/1986 | Gonser |
| 4,614,498 A | 9/1986 | Vaccaro |
| 4,634,376 A | 1/1987 | Mossle et al. |
| 4,676,749 A | 6/1987 | Mabille |
| 4,682,949 A | 7/1987 | Warrin |
| 4,735,200 A | 4/1988 | Westerman |
| 4,808,109 A | 2/1989 | Thornton |
| 4,818,229 A | 4/1989 | Vasile |
| 4,820,152 A | 4/1989 | Warrin et al. |
| 4,877,399 A | 10/1989 | Frank et al. |
| 4,928,675 A | 5/1990 | Thornton |
| 4,961,698 A | 10/1990 | Vlock |
| 4,975,058 A | 12/1990 | Woodward |
| 4,978,297 A | 12/1990 | Vlock |
| 5,039,304 A | 8/1991 | Heil |
| 5,040,978 A | 8/1991 | Falcon et al. |
| 5,062,797 A | 11/1991 | Gonser |
| 5,082,443 A | 1/1992 | Lohn |
| 5,088,924 A | 2/1992 | Woodward |
| 5,125,837 A | 6/1992 | Warrin et al. |
| 5,131,844 A | 7/1992 | Marinaccio et al. |
| 5,145,370 A | 9/1992 | Woodward |
| 5,190,456 A * | 3/1993 | Hasegawa .................... 433/120 |
| 5,211,531 A | 5/1993 | Kakimoto |
| 5,230,621 A | 7/1993 | Jacoby |
| 5,252,064 A | 10/1993 | Baum et al. |
| 5,311,632 A | 5/1994 | Center |
| 5,320,530 A | 6/1994 | Fong |
| 5,346,489 A | 9/1994 | Levy et al. |
| 5,378,150 A | 1/1995 | Harrel |
| 5,382,162 A | 1/1995 | Sharp |
| 5,395,240 A | 3/1995 | Paschke et al. |
| 5,419,703 A | 5/1995 | Warrin et al. |
| 5,467,779 A | 11/1995 | Smith et al. |
| 5,531,597 A | 7/1996 | Foulkes et al. |
| 5,567,153 A | 10/1996 | Foulkes et al. |
| 5,634,790 A | 6/1997 | Pathmanabhan et al. |
| 5,636,988 A | 6/1997 | Murayama |
| 5,653,643 A * | 8/1997 | Falone et al. ............... 473/300 |
| RE35,712 E | 1/1998 | Murayama |
| 5,716,210 A | 2/1998 | Novak |
| 5,743,718 A | 4/1998 | Mendoza et al. |
| 5,743,731 A | 4/1998 | Lares et al. |
| 5,749,727 A | 5/1998 | Dao et al. |
| 5,762,541 A | 6/1998 | Heath et al. |
| 5,775,901 A | 7/1998 | Riso |
| 5,776,155 A | 7/1998 | Beaupre et al. |
| 5,795,167 A | 8/1998 | Brenner |
| 5,810,588 A | 9/1998 | Cohen |
| 5,833,457 A | 11/1998 | Johnson |
| 5,836,762 A | 11/1998 | Peithman |
| D411,726 S | 6/1999 | Novak |
| 5,938,441 A | 8/1999 | Brenner |
| 5,967,779 A | 10/1999 | Brassil |
| 5,967,784 A | 10/1999 | Powers |
| 5,984,654 A | 11/1999 | Mendoza et al. |
| 6,030,212 A | 2/2000 | Schuman et al. |
| RE36,699 E | 5/2000 | Murayama |
| 6,062,858 A | 5/2000 | Hugo et al. |
| D427,682 S | 7/2000 | Novak |
| 6,106,288 A | 8/2000 | Brassil et al. |
| 6,106,289 A | 8/2000 | Rainey et al. |
| 6,123,268 A | 9/2000 | Chastine |
| 6,159,175 A | 12/2000 | Strukel et al. |
| 6,168,433 B1 | 1/2001 | Hamlin |
| 6,178,910 B1 | 1/2001 | Pollack |
| 6,179,617 B1 | 1/2001 | Ruddle |
| 6,186,783 B1 | 2/2001 | Brassil et al. |
| 6,206,694 B1 * | 3/2001 | Swan .......................... 433/88 |
| 6,214,023 B1 | 4/2001 | Whipple et al. |
| 6,293,795 B1 | 9/2001 | Johnson |
| 6,494,714 B1 | 12/2002 | Copeland |

FOREIGN PATENT DOCUMENTS

| | | |
|---|---|---|
| DE | 2 107 526 | 2/1971 |
| EP | 0 247 916 A1 | 12/1987 |
| EP | 0 366 624 A1 | 10/1989 |
| WO | WO 01/03601 A1 | 1/2001 |
| WO | WO 01/45581 A1 | 6/2001 |

OTHER PUBLICATIONS

KINETIC Instruments Inc. 1995 Product Specification Brochure, 3 pages.
Patterson Dental 1999 Catalog with Swivel Assembly for Handpieces, pp. 232, 233.
1999 Sullivan-Schein Dental Catalog, pp. 180, 181, 402 with swivel function for handpieces and sonic scalers.
1997 Partial Star Dental, pp. 1, 2, 4, 5, 7, 9, 10 and 13-20 with swivel function for handpieces and sonic scalers.
1992 Product Specification Brochure, Star Dental Sonic Scalers with Swivel, 2 pages.

1990 Star Dental Product Specification Brochure, Sonic Scaler with Swivel 2 pages.
EMS Pricelist 1998.
Amdent®brochure re Built-in scaler, 1998.
EMS Brochure re EMS Piezon Master 400, 1999.
EMS Brochure er miniPiezon®!, 1999.
EMS Brochure re Piezon® Master 400, Apr. 1999.
Satelec Brochure re Scaling Kit, 1998.
Satelec Brochure re Suprasson® P5 Booster, 1999.
Vista Dental Products advertisement re Select+, Jun. 1999.

* cited by examiner

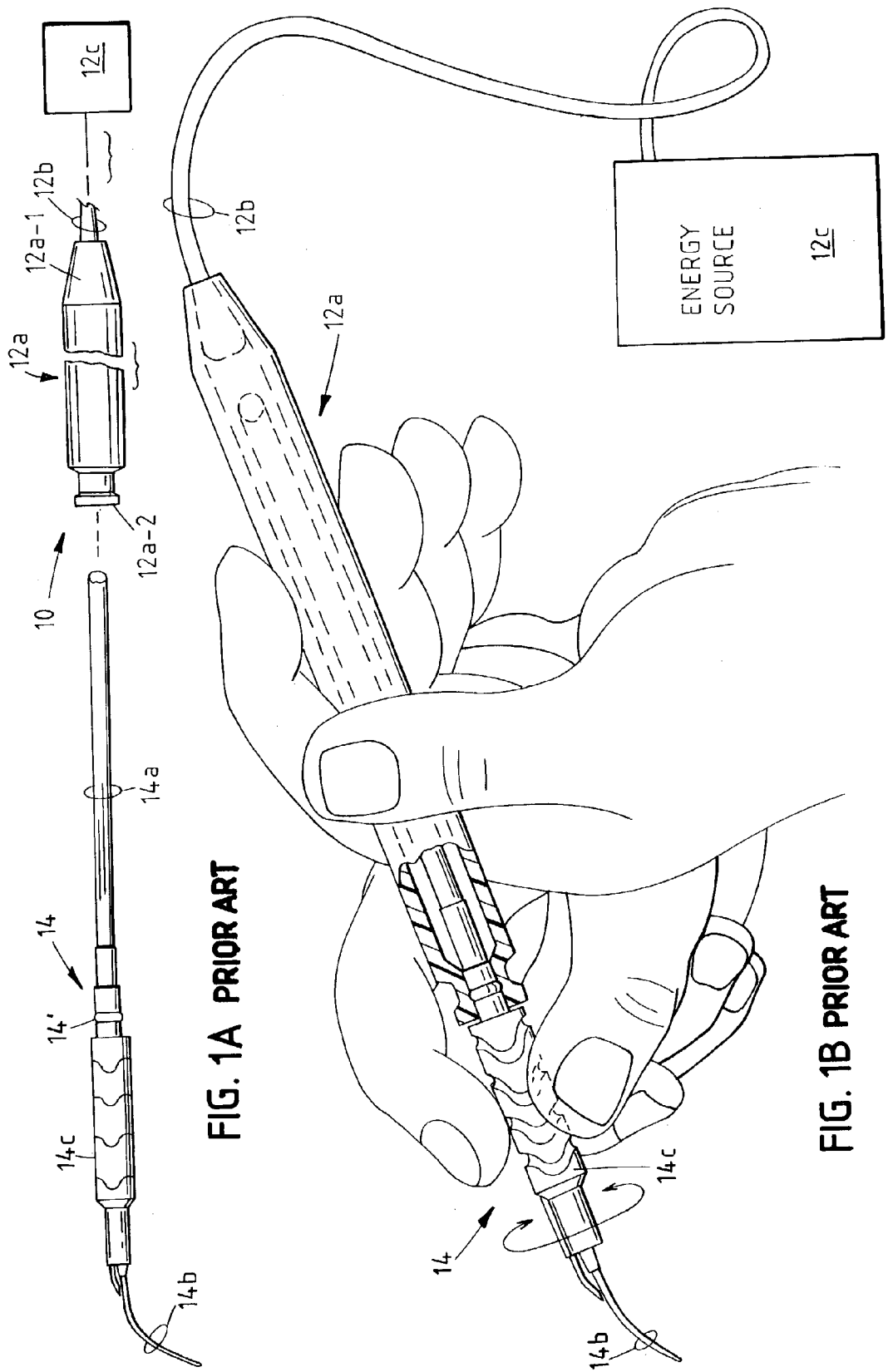

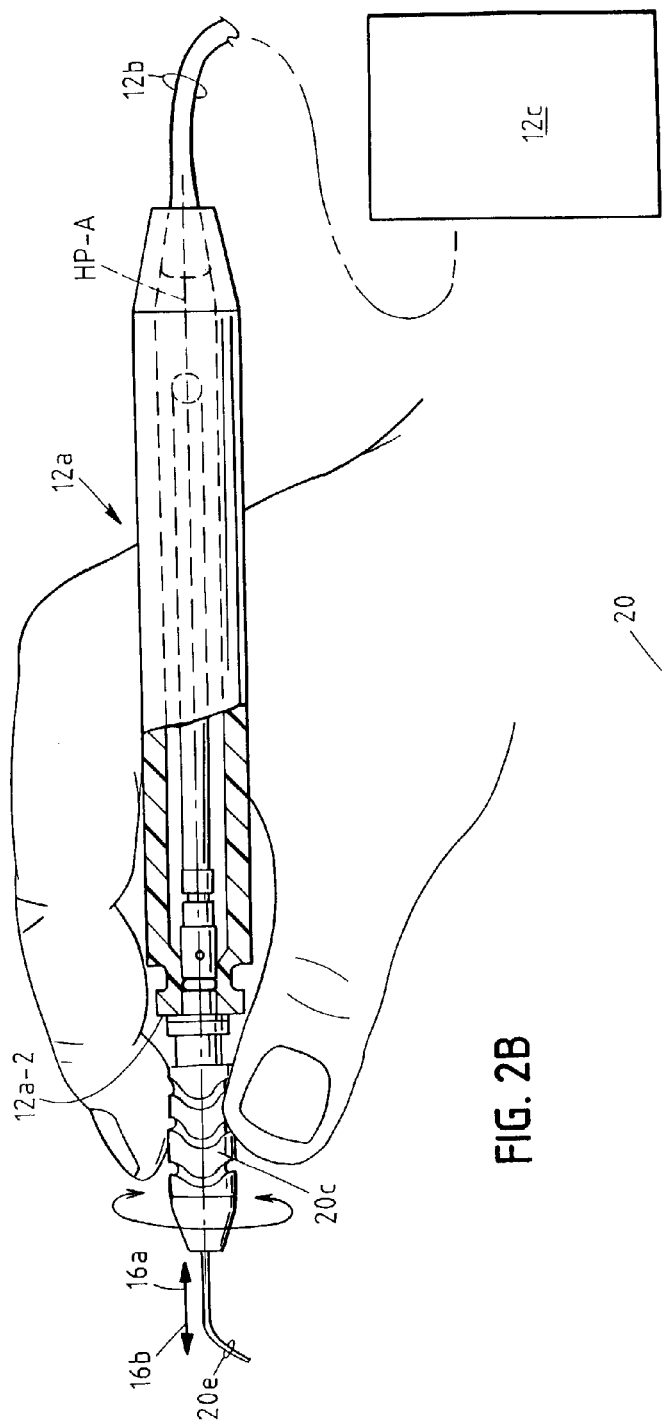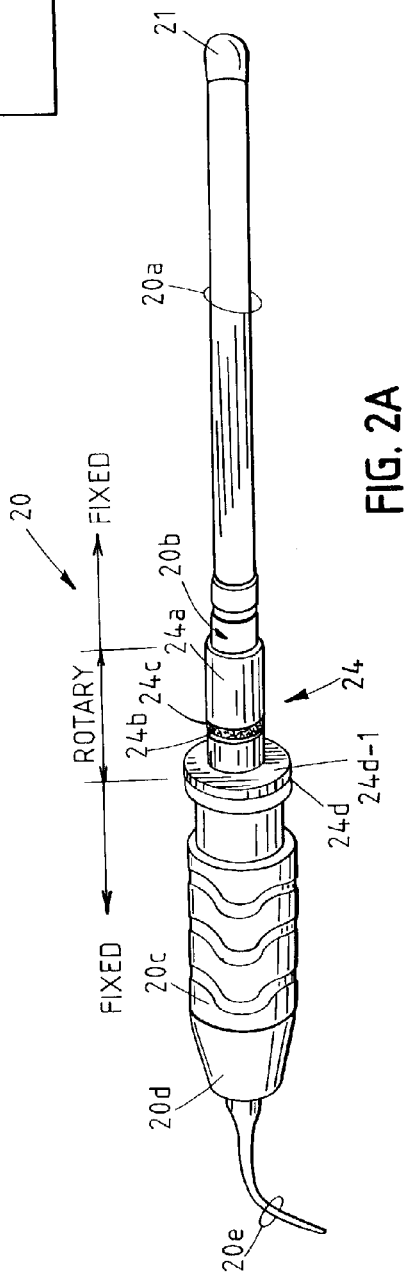
FIG. 2B
FIG. 2A

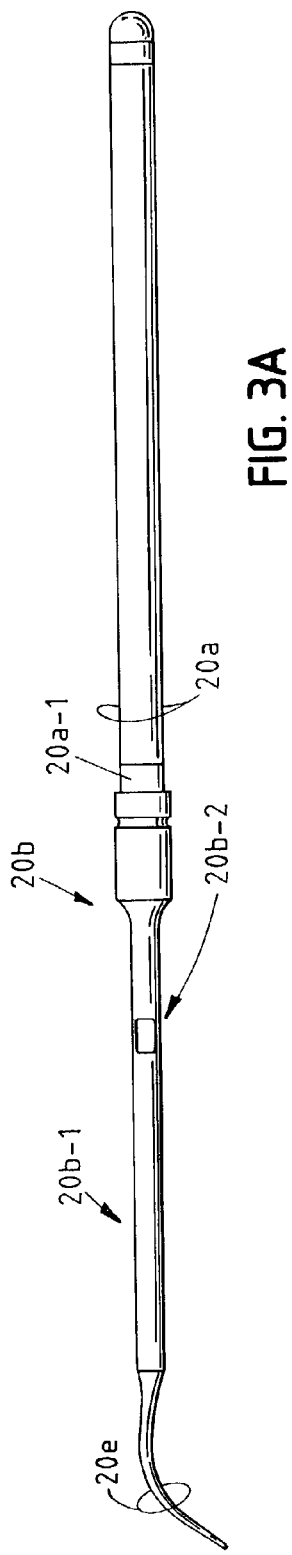
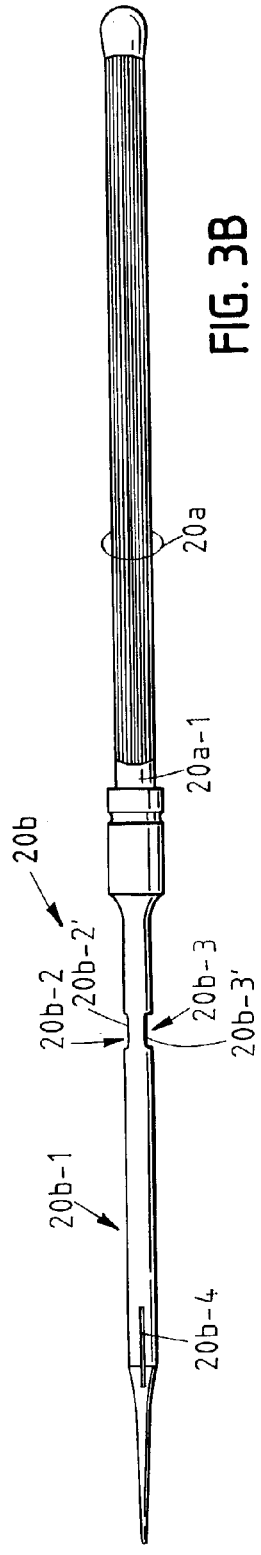
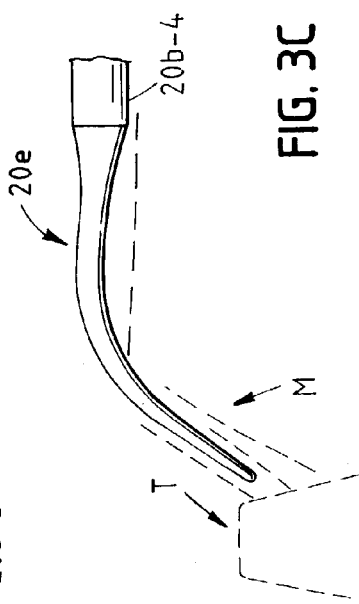

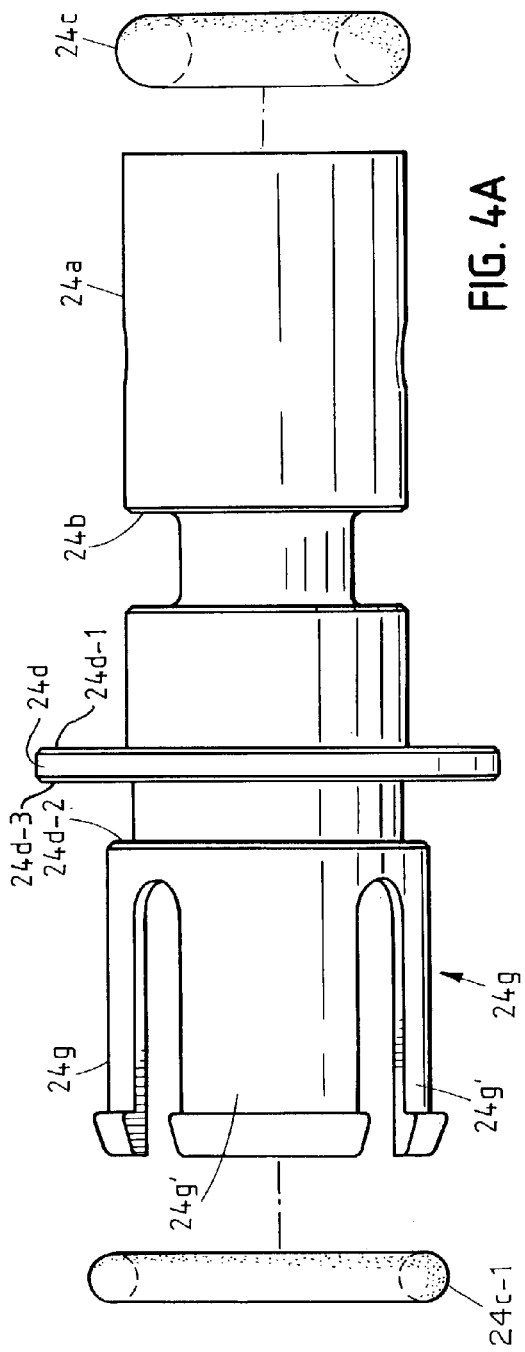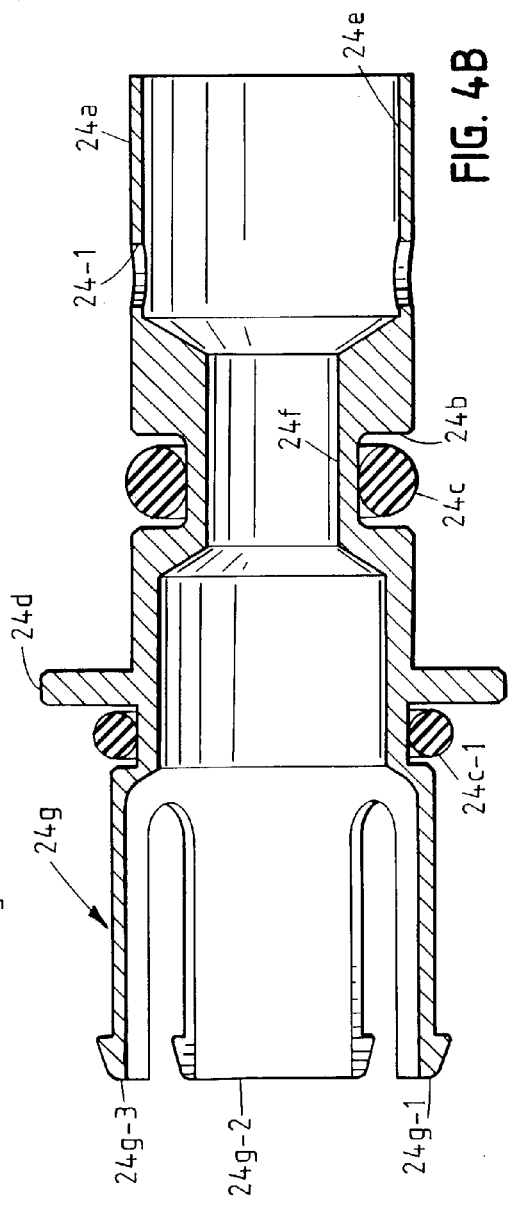

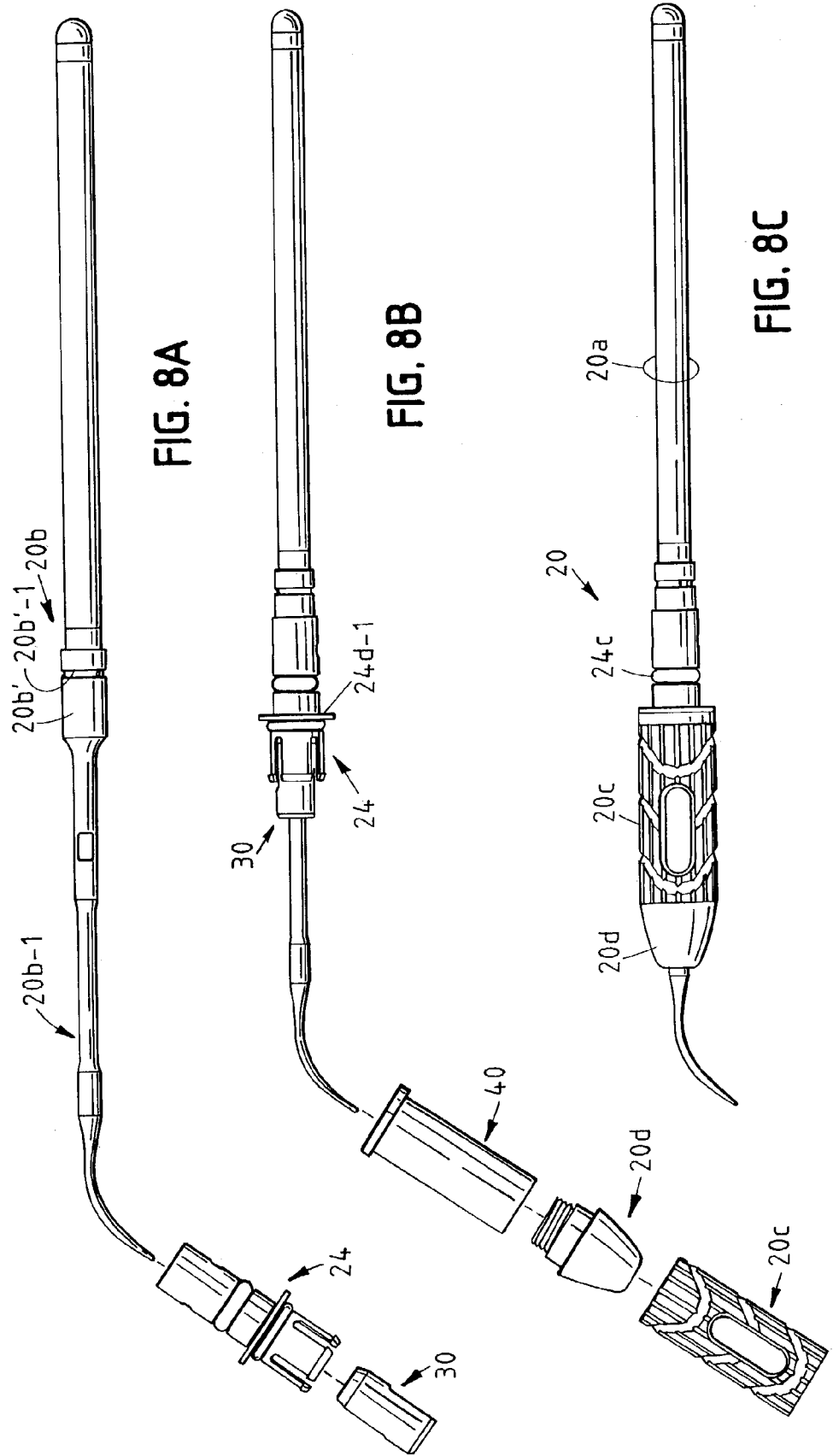

TWO PART ULTRASONIC SWIVEL INSERT, WITH ONE PART ROTATABLE RELATIVE TO THE OTHER

This is a Divisional Application claiming the benefit of the earlier filing date of Utility application Ser. No. 09/917,101, filed Jul. 27, 2001, now U.S. Pat. No. 6,716,028 which claimed the benefit of the earlier filing dates of Provisional Application Ser. No. 60/223,447, filed Aug. 4, 2000 and Ser. No. 60/270,687, filed Feb. 22, 2001.

FIELD OF THE INVENTION

The invention pertains to ultrasonic inserts of a type used in medical/dental treatments. More particularly, the invention pertains to such inserts with enhanced operating efficiency and user comfort.

BACKGROUND OF THE INVENTION

Ultrasonic scalers are used in dental offices for de-plaque-ing teeth. Unlike manual scalers, these instruments are powered i.e., the tip of the instrument vibrates at an ultrasonic frequency allowing quick and easy debridement. The operator has less hand fatigue as most of the energy for removing the plaque comes from the generator that powers the instrument. The dental practitioner need only lightly touch the tip of the instrument at an angle to the tooth surface to dislodge the plaque.

Known ultrasonic scalers, such as scaler 10 illustrated in FIG. 1A, have a handpiece 12a coupled at one end 12a-1 to a cable 12b which includes a hose, to provide a fluid, and conductors to provide electrical energy. The other end of the cable 12b terminates at an electrical generator and fluid source 12c. One type of fluid is water.

The other end of the handpiece 12a-2 is hollow and is intended to receive a replaceable insert 14 with a transducer 14a (magnetostrictive or piezoelectric) carried on the insert. The transducer 14a extends from a proximal end of the insert 14 into the hollow body 12a-2. An ultrasonically vibrated tip 14b extends from a distal end of the insert. One such insert has been disclosed and claimed in U.S. Pat. No. 5,775,901, entitled "Insert For Ultrasonic Scaler", incorporated herein by reference.

Known magnetostrictive ultrasonic inserts function by exciting a stack of thin nickel plates at a frequency equal to the stack's natural frequency. The excitation is induced through an electrical generator in unit 12c, which supplies a current to a coil embedded in the handpiece. When the insert 14 is placed in the handpiece 12a and the frequency generator 12c is powered on, the operator tunes the generator (manual tuning) until it reaches the resonance frequency i.e., attains the natural frequency of the insert. Alternately, autotune units automatically lock on the insert resonance frequency once powered on. At this time, the stack starts vibrating. This vibration of the stack is amplified and transmitted to the tip 12b by means of a connecting body or concentrator. The connecting body is made from material that provides good sound transmission efficiency.

While the insert 14 is operational, fluid is pumped through the cable-generator system 12b, c and through the handpiece 12a to the tip 14b of the insert 14. The vibrating tip 14b breaks the fluid stream into a spray. The spray not only keeps the tip cool, but also keeps the surface of the tooth cool and provides protection against tissue damage.

The fluid path through the handpiece 12a needs to be sealed such that no leakage occurs until the fluid stream exits from the insert at the very tip through a fluid delivery channel. Typically, ultrasonic inserts do not have any moving parts other than the minuscule displacement of the nickel stack, the connecting body or the tip.

Known magnetostrictive dental scaling ultrasonic inserts used in the U.S.A. are designed to vibrate at 25 kHz or 30 kHz frequencies. Another system, popular in Europe, uses a piezoelectric transducer.

In using an ultrasonic scaler during a cleaning, the dental practitioner will need to repeatedly re-orient the location of the insert tip 14b with respect to tooth surface depending on which tooth of the mouth is being cleaned. In making this angular adjustment, as illustrated in FIG. 1B, the practitioner will typically take the insert out of the patient's mouth, rotate the insert 14, and tip 14b, inside the handpiece 12a locating tip 14b at a desired angular position. Both hands are used for this rotation as the frictional forces that produce a tight fit of the insert 14 in handpiece 12a must be overcome. During a typical treatment, the process of reorienting the tip must be carried out numerous times. This is not only time consuming but also interrupts the ease and smooth flow of work.

In areas of the mouth where the practitioner chooses not to rotate the insert 14, the practitioner's wrist must be twisted sufficiently to achieve the same function. This twisting action is opposed by the resistance of the cable 12b, the fluid supply hose and power conductors, which is attached to the handpiece 12a.

There continues to be a need for ultrasonic scalers which are more comfortable and less fatiguing to use than known instruments. Preferably, any improvements will be downwardly compatible with the numerous generators and handpieces that are already present in dental offices.

SUMMARY OF THE INVENTION

A rotatable ultrasonic insert has a body section which carries a bearing for rotatably engaging an ultrasonic handpiece. The body is rotatable, about an axial centerline.

Rotation can be effected by applying a force only to the insert. In response, the insert rotates but the handpiece does not. Hence, single handed, two finger rotation is possible.

Preferably, a swivel feature is located at the gripping region of the insert, i.e., close to the treatment tip, where the practitioner would typically position his or her fingers. The swivel allows the insert to rotate 360 degrees without any limitation. This enables the practitioner to position the insert, and the tip, at any angular orientation without having to take the insert out of the patient's mouth. The swivel also allows rotation of the gripping region and tip without having to rotate the handpiece and/or the supply cord. This removes the resistance from the operator's hand and reduces hand fatigue.

Additionally, a large diameter grip or handle, not only reduces finger fatigue but also transmits a larger torque to the swivel feature for the same amount of force.

An elastomeric handle, carried by the body, comfortably interfaces with a user's fingers. The user can rotate the elastomeric handle and the insert with two fingers relative to the handpiece. Hence, during treatment there will be no need to rotate the handpiece.

The elastomeric material allows for a positive grip since it deforms under finger pressure and becomes locally non-cylindrical in shape. The preferred material is silicone. Silicone is not only repeatedly sterilizable under most sterilization processes found in dental offices but also provides good traction with respect to the type of gloves which are commonly used in dental offices.

The elastomeric handle engages the body only at a region of minimal ultrasonically induced, vibration. The limited connectivity between the body and the elastomeric handle minimizes build up of heat between the body and that handle. It also avoids damping ultrasonic vibrations transmitted along the body.

A method of assembly includes:
providing a body which carries an ultrasonic transducer, at one end, and, a displaced treatment applying tip at the other end;
sliding a rotary handle past the treatment applying tip toward the bearing;
connecting the handle to the body at a region of minimal ultrasonic vibration.

In another aspect of the invention, an adaptor has an external periphery which can be slidably and releasibly inserted into the opening in the handpiece. A standard ultrasonic insert is inserted through the adaptor into the handpiece. The insert can then be rotated relative to the handpiece with a rotational force applied only thereto. Alternatively, the adaptor can be snap fitted onto an exterior periphery of a handpiece.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 1A illustrates a prior art ultrasonic scaler having an insert and handpiece;

FIG. 1B illustrates one aspect of usage of the prior art insert/handpiece combination of FIG. 1A;

FIG. 2A illustrates an insert in accordance with the present invention;

FIG. 2B illustrates the insert of FIG. 2A in a handpiece as in FIG. 1A and aspects of usage thereof;

FIGS. 3A, B and C are various views of an ultrasonic insert body in accordance with the present invention;

FIGS. 8A, B and C illustrate steps in assembling an insert in accordance with the present invention;

DETAILED DESCRIPTION OF THE PREFERRED EMBODIMENTS

Figure 4D:
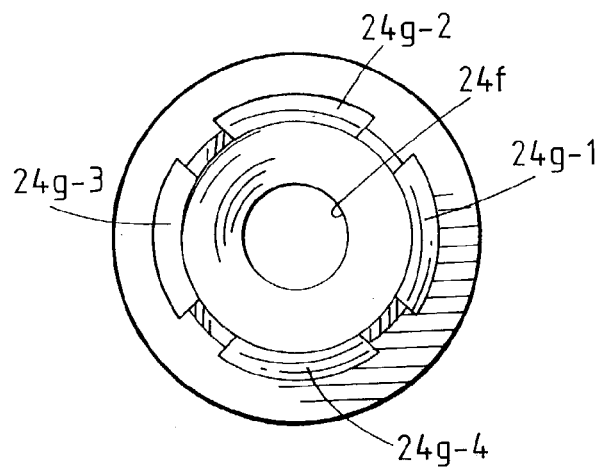
FIGS. 4A, B, C and D are various views of a snap-fit rotary bearing usable with the body of FIG. 3A.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

FIG. 2A illustrates an insert 20 in accordance with the present invention. The insert 20 includes a transducer 20a which is illustrated as a magnetostrictive transducer. Alternately, it could be a piezoelectric ultrasonic transducer without departing from the spirit and scope of the present invention.

The transducer is rigidly coupled to an elongated body 20b which is covered in part by a cylindrical, elongated deformable elastomeric grip 20c. The grip 20c terminates in a cone 20d which is positioned between the grip 20c and operative treatment applying tip 20e.

The insert 20 operates in accordance with the principals of known ultrasonic dental instruments as discussed above relative to FIG. 1A. However, insert 20 also carries a rotary bearing 24 which exhibits a hollow cylindrical stem section 24a which defines a cylindrical region 24b which receives a sealing O-ring 24c. The hollow member 24a terminates at a disc 24d of larger diameter. A planar surface 24d-1 of disk 24 is adjacent to stem 24a As discussed subsequently, when installed on the elongated body 20b, the rotary bearing member 24 is rotatable relative to the body 20b, gripping member 20c and tip 20e. Hence, if the member 24 is fixed, the body 20b, gripping member 20c and tip 20e are readily rotatable therein.

FIG. 2B illustrates the standard ultrasonic handpiece 12a, cable 12b and generator 12c, discussed above, of a type found in dental offices. The insert 20 is slidably receivable, in a direction 16a, in the hollow end 12a-2 of the handpiece 12a.

The cylindrical stem 24a of the rotary bearing 24 slides into the hollow handpiece 12a. The O-ring 24c slidably engages the interior periphery of the handpiece 12a providing a fluid seal and reliably engaging the insert 20 with the handpiece 12a.

When installed in the handpiece 12a, as illustrated in FIG. 2B, insert 20 can be rotated relative to handpiece 12a with rotary forces applied to the deformable gripping member 20c for purposes of orienting the tip 20e relative to a tooth being de-plaqued. As illustrated in FIG. 2B, the practitioner need not restrain the handpiece 12a while rotating the insert 20. Additionally, insert 20 is relatively rotatable relative to handpiece 12a using only two of the practitioner's fingers. Thus, the orientation of the tip 20e can be continuously altered with only two of the practitioner's fingers, requiring only one hand, while the scaling operation proceeds. This will reduce operator fatigue and substantially shorten the time necessary for the scaling process. The expected torque needed to rotate insert 20 preferably will be less than 2.0 inch-oz.

When the practitioner has concluded the de-plaqueing process, the insert 20 can be removed from the handpiece by pulling it axially from the handpiece in a direction 16b and sterilized. The same insert or a different insert can then be subsequently inserted into handpiece 12a to treat the next patient. It will be understood that the present invention is applicable to ultrasonic inserts which utilize either magnetostrictive or piezoelectric transducers without limitation.

FIGS. 3A, 3B, 3C illustrate different views of the body 20b of the insert 20. As illustrated in FIGS. 3A and 3B, body portion 20b is attached to a first end 20a-1 of transducer 20a as would be understood by those of skill in the art. An elongated cylindrical extension 20b-1 extends axially from transducer 20a toward tip 20e.

The elongated cylindrical metal member 20b-1, as would be known to those of skill in the art, is caused to vibrate axially, in response to electro-magnetic signals received at transducer 20a from handpiece 12a. The signals are produced by generator 12c. This axial ultrasonic vibration is in turn coupled to the tip 20e and used for effecting de-plaqueing of the subject tooth T, in a spray of fluid M, illustrated in phantom in FIG. 3C.

A pair of notches 20b-2, 20b-3 is formed on elongated body member 20b-1 in a region of substantially zero axial ultrasonic vibration. While a pair of notches 20b-2, -3 has been illustrated in FIG. 3B, it will be understood that a single notch, or three notches could be used without departing from the spirit and scope of the present invention. Additionally, the exact shape of the generally rectangular notches 20b-2, -3 is not a limitation of the present invention.

An interior or base plane 20b-2', 20b-3' of each notch 20b-2, -3 is parallel to a plane through the central axis of tip 20e. This notch/tip configuration facilitates energy transmission along insert 20 without increasing the risk of a mechanical fracture due to potential fatigue stress.

An elongated fluid flow slot 20b-4 extends axially in the region where the body 20b-1 interfaces with the tip 20e. As discussed subsequently, fluid for the spray M flows therethrough.

FIGS. 4A, B, C and D illustrate different views and additional details of rotary bearing 24. As illustrated therein, the cylindrical stem 24a is hollow and defines an interior peripheral surface 24e which is adjacent to the elongated body portion 20b, see FIG. 2A. The bearing member 24 carries a second O-ring 24c-1 in a cylindrical region 24d-2 which is adjacent to a plurality of radially disposed spring-loaded fingers indicated generally at 24g.

The fingers 24g each terminate at a barbed free end, such as 24g-1, -2, -3 with preferably four such fingers disposed radially about the annular surface 24d-2. Neither the number nor the exact shape of the ends 24g-1, -2 . . . -n are limitations of the present invention. As discussed in more detail subsequently, the fingers 24g-1, -2, -3, -4 are deflectable radially inward during assembly and are biased radially outwardly to return to their undeflected condition, illustrated in FIG. 4A, 4B.

Figure 4C:
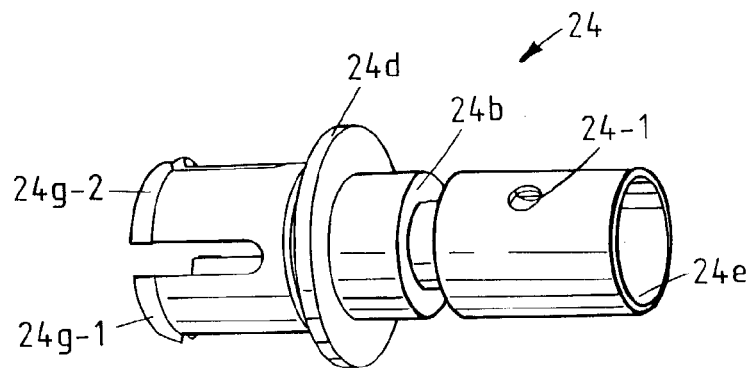
Figure 5A:
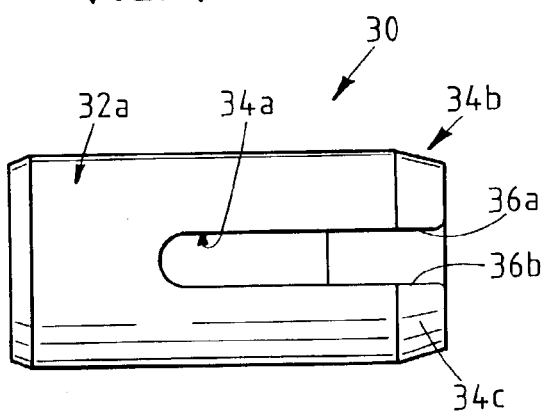
FIGS. 5A, B, C and D are various views of a torque lock in accordance with the present invention.
Figure 5B:
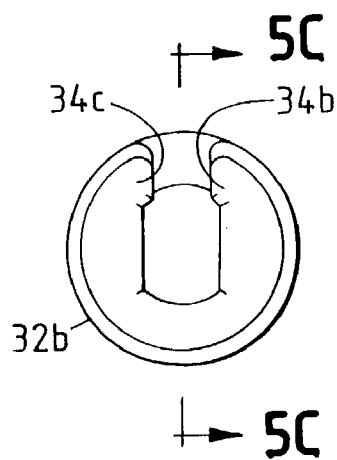
Figure 5C:
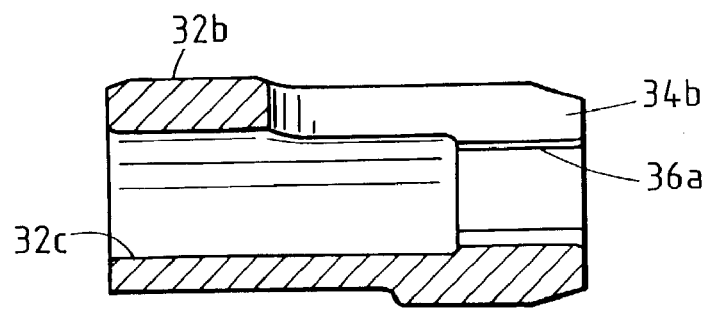
Figure 5D:
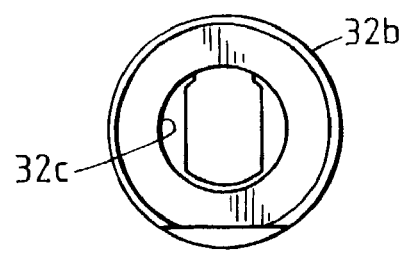

The second O-ring 24c-1 which is positioned adjacent annular surface 24d-2 cooperates with O-ring 24c to provide a sealed fluid flow path between handpiece 12a and cone 20d. Cooling fluid flows from handpiece 12a through aperture 24-1, FIG. 4c, and past the fingers 24g-1, -2, -3, -4. It will be understood that the number of fingers 24g is not a limitation of the present invention.

FIGS. 5A–5D illustrate various views of a torque lock 30 which couples a torque due to force applied to deformable gripping member 20c by the user's fingers to the body 20b and treatment tip 20e. The torque lock 30 is preferably molded of a sterilizable thermoplastic which, as discussed below, permits it to deform during assembly without fracturing.

The torque lock 30 has a hollow body section 32a with an exterior periphery 32b and an internal circumferential periphery 32c. The torque lock is molded with a slot 34a formed in the body 32a which permits outward radial deformation of sections 34b and 34c, adjacent the slot 34a, as the torque lock 30 is slid onto the elongated body portion 20b-1. Surfaces 36a, 36b slidably engage the notches 20b-2, -3 of the elongated member 20b-1. When the notches are so-engaged, the deformable members 34b, c move radially inwardly to a non-deformed condition. In this state, torque lock 30 is locked to the body 20b at the notches 20b-2, -3.

The interaction between the surfaces 36a, b, in the slots 20b-2, -3 inhibits both rotation and translation of the torque lock 30 relative to the body member 20b-1. Hence, rotating the torque lock 30 will also rotate the body 20b of the insert.

Once the torque lock 30 has been installed on the body member 20b-1 at the slots 20b-2, -3, it will be fixedly located at a region of substantially zero axial ultrasonic vibration. This minimizes a build-up of heat between the vibrating body 20b-1 and the torque lock 30. As will be understood by those of skill in the art, in addition to locating the notches 20b-2, -3 at a region of minimal axial ultrasonic vibration, preferably centered on the expected nodal point of zero vibration, the cross section of the connecting body portion 20b-1 through the notches 20b-2, -3 will have a large enough cross-sectional area to transmit ultrasonic vibrations without constriction.

Figure 6A:
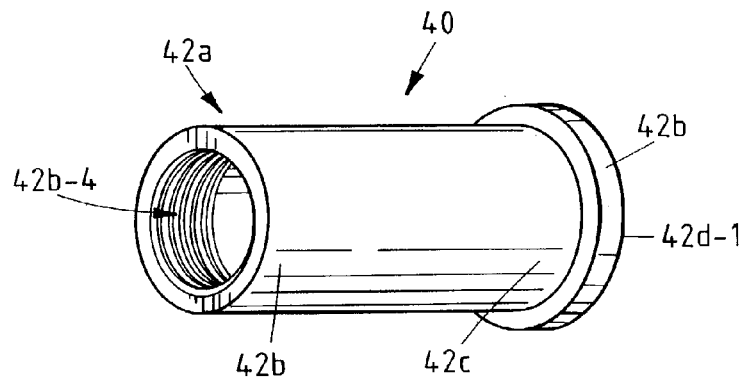
FIGS. 6A, B and C are various views of a swivel housing in accordance with the present invention.
Figure 6B:
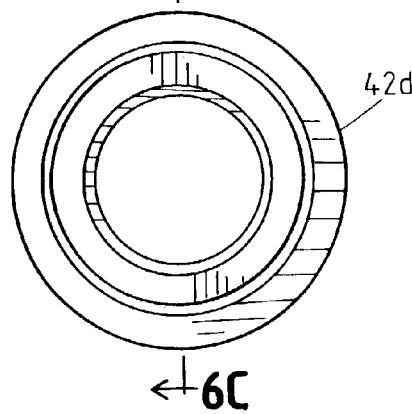
Figure 6C:
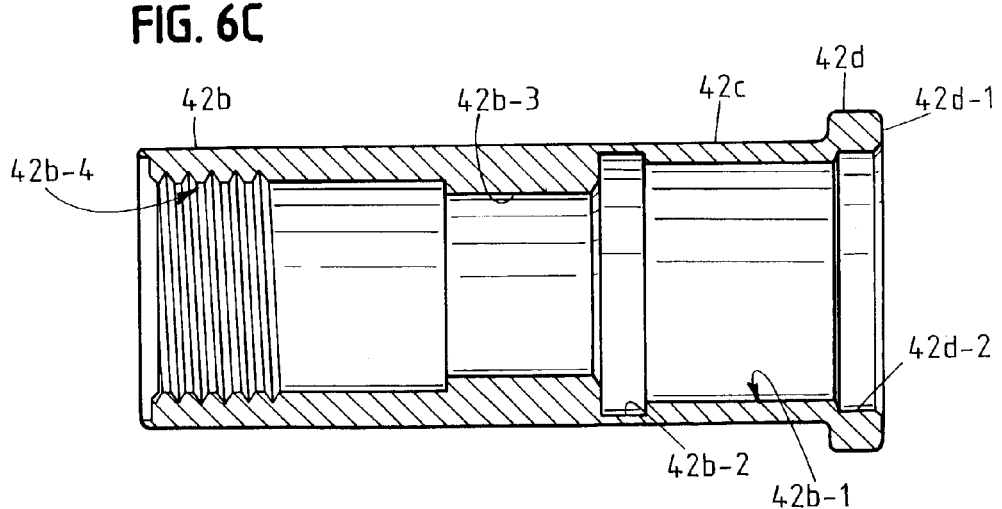

FIGS. 6A, B, C illustrate various views of a housing 40 which is press fit over torque lock 30 and which slidably and lockingly engages barbed fingers 24g-1, -2, -3, and -4 of the rotary bearing 24. The housing 40 has an elongated generally cylindrical body 42a with a smooth exterior periphery 42b. The body 42a terminates at an end 42c adjacent an annular shoulder 42d.

The shoulder 42d in turn has an end surface 42d-1. When installed, the end surface 42d-1 is adjacent to and rotates relative to annular surface 24d-3 of bearing 24.

The annular member 42d exhibits an internal cylindrical peripheral surface 42d-2 which traps O-ring 24c-1 in position, forming a fluid seal with bearing 24 when surface 42d-1 is positioned adjacent to surface 24d-3. When so-positioned, the housing 40 can rotate relative to bearing 24 but is not movable axially relative thereto.

When the housing 40 is rotated relative to the bearing 24, the surface 42d-2 slides over O-ring 24c-1 without excessive friction thereby enabling a practitioner to rotate the tip 20e relative to the handpiece 12a with the use of force applied to elastomeric gripping member 20c by only two fingers.

The housing 40 has an interior, cylindrical peripheral surface 42b-1 which surface deflects the barbed fingers 24g-1, -2, -3, -4 radially inwardly when the housing 40 is slid onto the fingers 24g. The fingers 24g, which have been inwardly radially deflected by the surface 42b-1 engage a cylindrical slot 42b-2 with a snap fit. The radially compressed fingers 24g expand outwardly radially and the barbed ends 24g-1, -2, -3, -4 lock into the slot 42b-2 precluding axial motion of the housing 40 away from surface 24d-3 of bearing 24.

As the housing 40 is slidably engaging the barbed fingers 24g-1, -2, -3, -4 and internal cylindrical peripheral surface 42b-3 engages exterior cylindrical peripheral surface 32b of torque lock 30 with a press or interference fit. The press fit between torque lock 30 and housing 40 locks those two parts together precluding either axial linear movement or rotary movement therebetween. The end 42b of housing 40 carries a plurality of threads 42b-4.

The snap fit between the housing 40 and the rotary bearing 24, in combination with the O-ring 24c-1 provide a sealed fluid flow path from inflow periphery 24e of bearing 24 through outflow end surface 42b-5 of housing 40. This fluid flow seal, as noted above, precludes fluid leakage. The exterior cylindrical surface 24g' of each of the fingers 24g rotatably engages the internal cylindrical surface 42b-1 of the housing 40. This provides a pair of rotatable bearing surfaces which permit smooth two finger rotation of the deformable member 20c and the treatment tip 20e. A medically acceptable, sterilizable, lubricant is preferably provided between the bearing surfaces to improve rotational smoothness and further reduce friction and required torque.

Figure 7A:
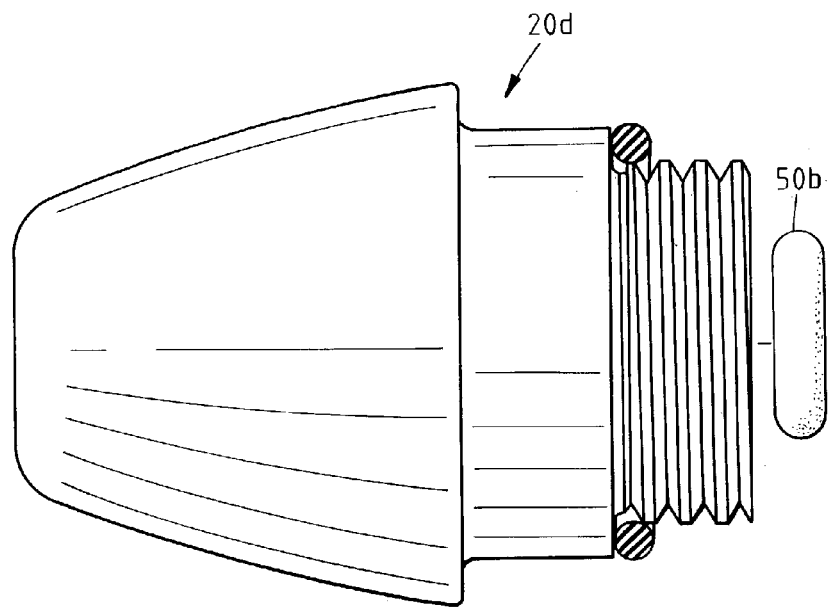
FIGS. 7A, B are various views of a cone usable in an insert in accordance with the present invention.
Figure 7B:
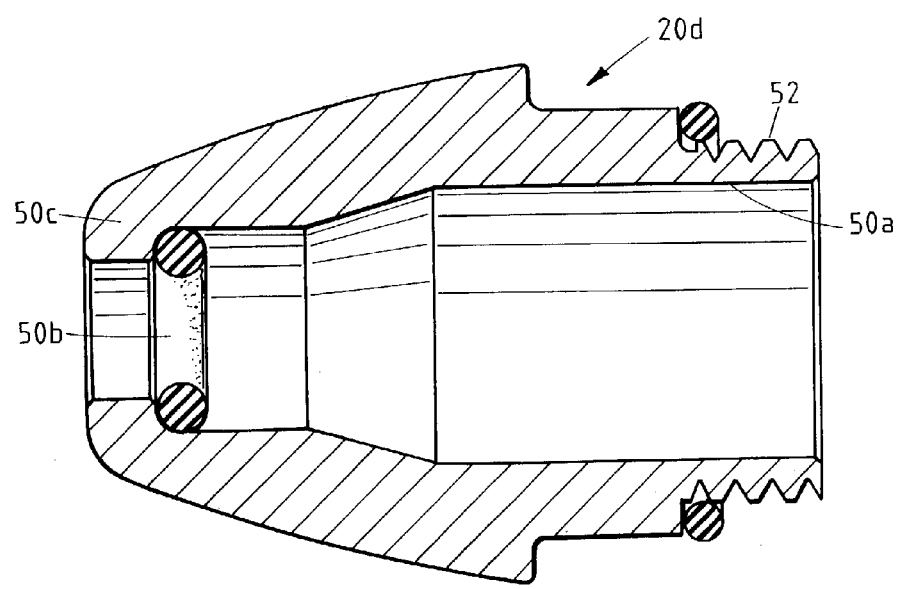

FIGS. 7A and 7B are views of cone 20d which is carried by rotatable housing 40. Cone 20d has an internal flow path 50a which is sealed by O-ring 50b. Cone 20d includes a set of threads 52. Cone 20d is coupled to housing 40 by the rotatable engagement of threads 42b-4 of housing 40 and 52 of cone 20d.

The O-ring 50b precludes leakage between an end 50c and a region of body portion 20b-1 which extends therethrough. Fluid exits cone 20d via fluid flow channel 20b-4 in the body portion 20b-1. Fluid exits the cone 20d in the channel 20b-4 as a stream. The stream of fluid impacts the vibrating tip 20e and creates a smooth spray pattern M suited for cooling and cleaning tissues. Adhesives, such as epoxy, can be used to permanently attach the cone 20d to the housing 40.

FIGS. 8A, 8B and 8C illustrate the steps of assembly of the insert 20. Groove 20b'-1 in body section 20b' provides a positive gripping surface usable during assembly by manufacturing fixtures to block axial movement of the insert 20.

As illustrated in FIG. 8A, initial steps of assembly of the insert 20 include sliding rotary bearing member 24 past operative tip 20e onto body portion 20b-1. The torque lock 30 is then slid onto the operative element 20e and forced along the elongated body 20b-1, which in turn forces elements 34b, c radially outward until surfaces 36a, b thereof slidably engage the slots 20b-2, -3. This slidable engagement with the slots in the body member 20b locks the torque lock 30 to the body member 20b and traps the bearing member 24 against a portion 20b' of the body 20b precluding axial movement thereof. The bearing member 24 continues to be rotatable relative to the elongated body portion 20b.

As illustrated in FIG. 8B, the housing 40 is then slid onto and past the operative element 20e and forced onto the rotary bearing 24, thereby radially inwardly deflecting the barbed fingers 24g-1, -2, -3, -4 and also press fit onto external peripheral surface 32b of torque lock 30 adjacent to disc 24d. When seated on the bearing member 24, the inwardly deflected fingers 24g expand into radial slot 42b-2, axially locking the housing 40 to the bearing 24 while still permitting relative rotary motion therebetween.

The circular elastomeric gripping member 20c can be slid onto housing 40 either before or after the cone 20d is threadably engaged therewith. The gripping region 20c has an inner diameter which is slightly smaller than the outer diameter of the housing 40. The member 20c thus elastically attempts to contract around the housing 40 which minimizes unintended slippage of the grip 20c relative to the housing 40. Member 20c can also be permanently attached to housing 40 with adhesive.

Figure 9A:
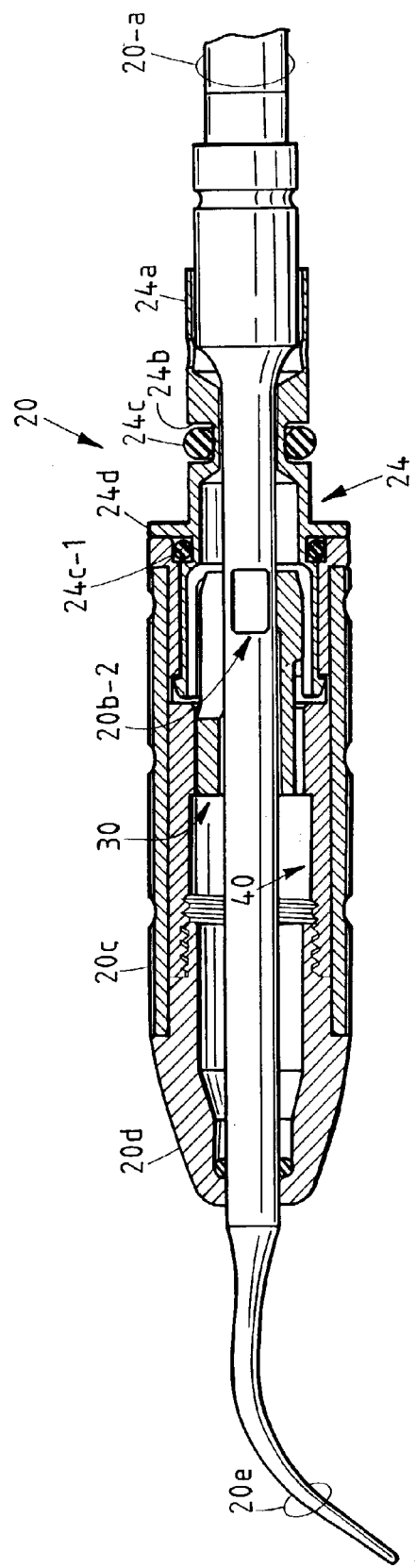
FIG. 9A is a side sectional view of an insert in accordance with the invention illustrating the relationship of various elements assembled in the steps of FIGS. 8A, B and C.
Figure 9B:
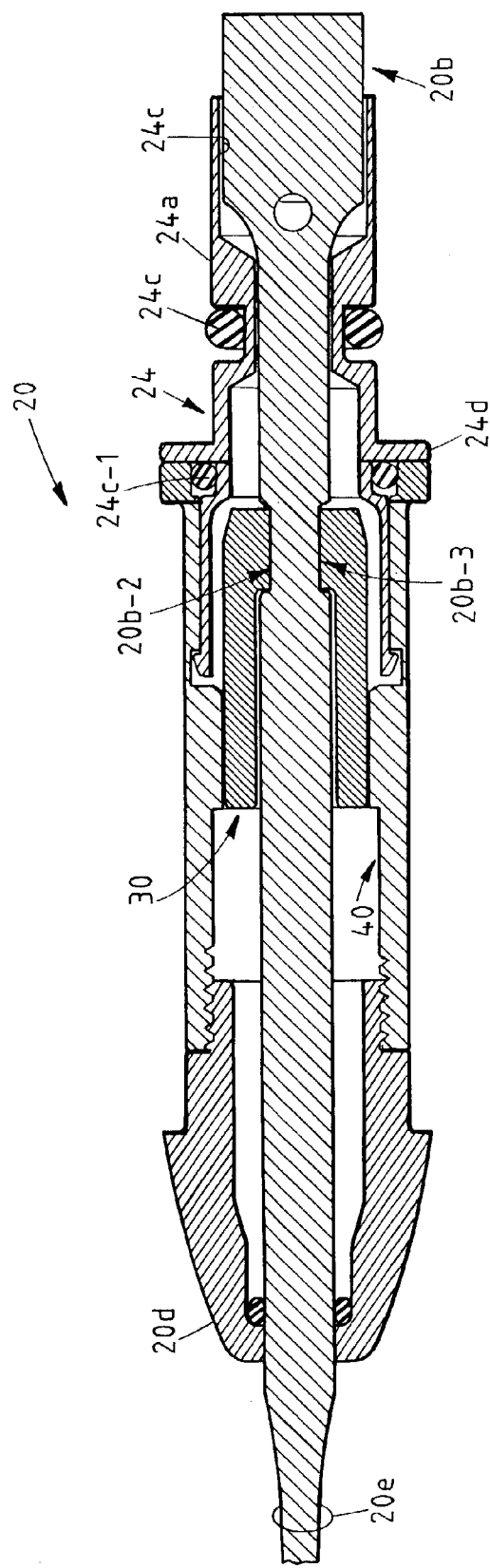
FIG. 9B is an enlarged sectional view illustrating aspects of a section of FIG. 9A.

FIG. 9A illustrates a side sectional view of an assembled insert 20 in accordance with the method of steps of FIGS. 8A, B and C. FIG. 9B is an enlarged side sectional view of a portion of FIG. 9A further illustrating the relationships of the various elements therein.

As will be understood by those of skill in the art, preferably tip 20c will be formed and heat treated prior to the start of the assembly process illustrated in FIG. 8A. By forming housing 40 as a separate element from core 20d, the length of each is less than the combined length of 20d and 40. Hence, each can be independently slid over exemplary curved tip 20e though the assembled combination 20d and 40 will not slide over tip 20e.

Figure 10A:
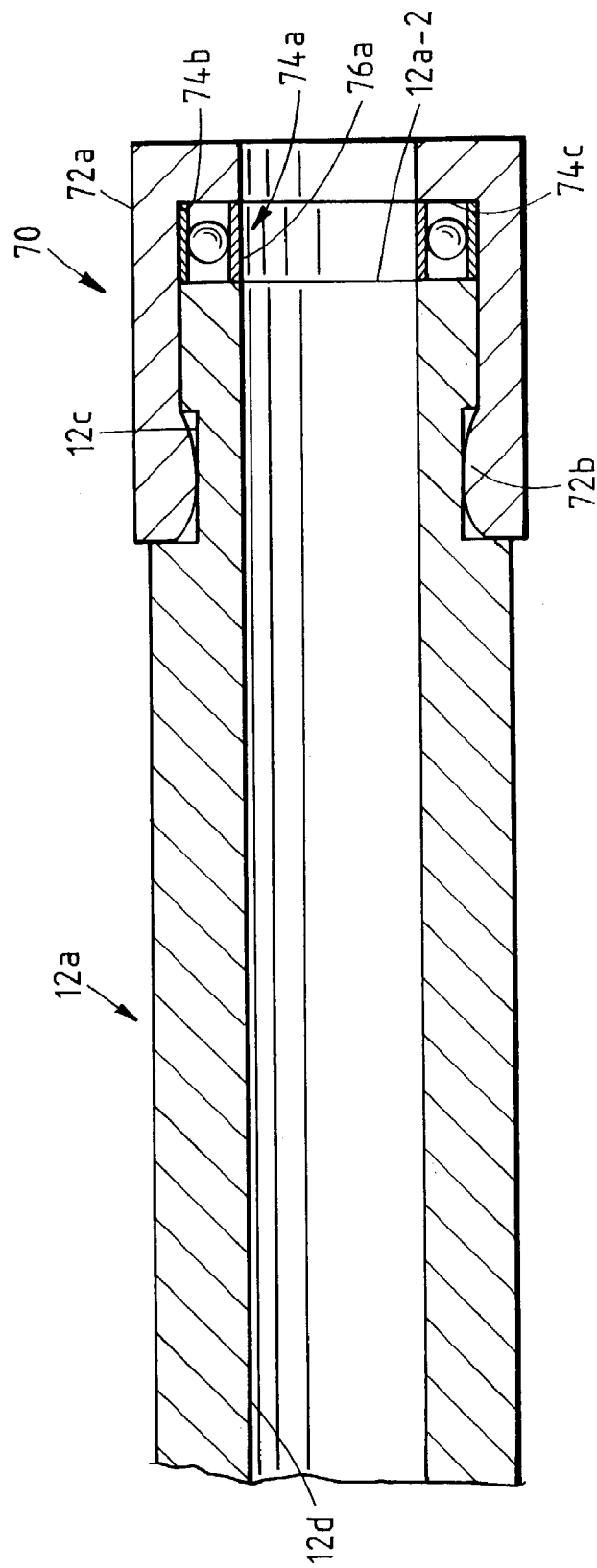
FIG. 10A is a side sectional view of a handpiece carrying a snap-on adaptor in accordance with the present invention.

FIG. 10A illustrates a snap-on plastic adaptor 70 which is intended to be used with a standard handpiece, such as the handpiece 12a. As illustrated in FIG. 10A, handpiece 12a includes an annular depression 12c adjacent to open end 12a-2. The adaptor 70 snap-fits onto the handpiece 12a at the groove 12c.

Adaptor 70 has a body section 72a which carries an annular locking protrusion 72b which slidably engages the slot 12c locking the adaptor 70 thereto. The adaptor 70 also includes a bearing 74a which is carried in an interior region 74b of the body 72a. An O-ring seal 74c can be positioned adjacent to the bearing 74a to minimize the likelihood of leakage from fluid flowing through the handpiece 12a into an insert coupled thereto.

The insert 70 defines a channel 76a which co-extends with and abuts channel 12d in handpiece 12a. The channels 76a and 12d receive a standard insert such as the insert 14, which is to be rotatably coupled to handpiece 12a and to be energized thereby.

Figure 10B:
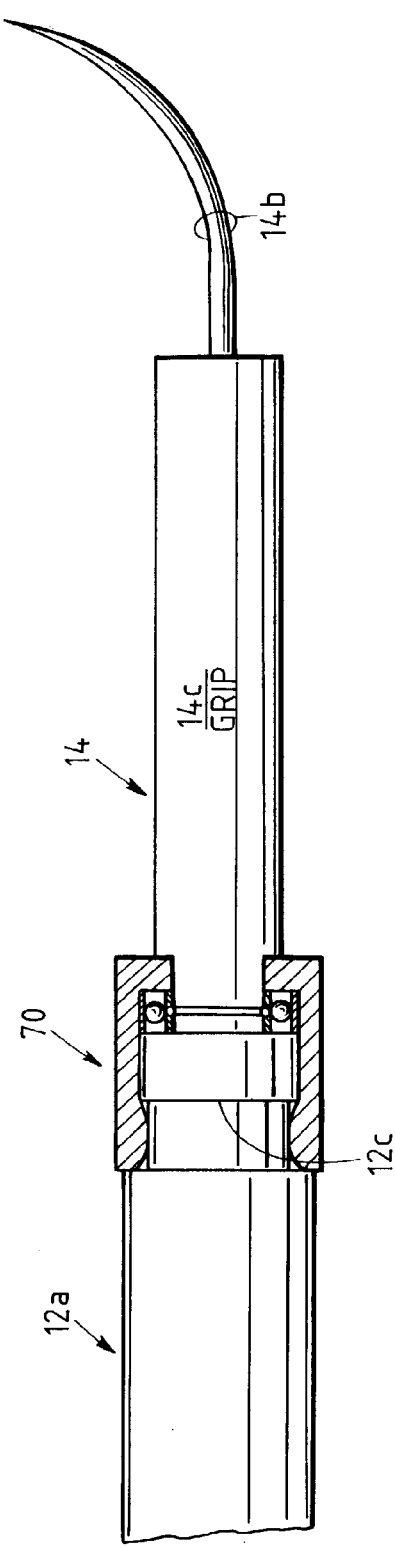
FIG. 10B is an enlarged partial side view of the handpiece and adaptor of FIG. 10A with a conventional ultrasonic insert positioned therein.

FIG. 10B illustrates added details of standard insert 14 coupled to adaptor 70 for rotation relative to handpiece 12a. In the embodiment illustrated in FIG. 10B, the adaptor 70 in combination with handpiece 12a and insert 14 provide a sealed fluid flow path between the interior peripheral surface 12b of the handpiece and tip 14b of the insert. In this configuration, a user can rotate insert 14 relative to handpiece 12a by applying rotary forces to the grip 14c in a manner analogous to the way in which rotary forces are applied to the grip 20c of rotatable insert 20 previously described.

Using insert 70, a standard handpiece, in combination with standard inserts, such as the insert 14, can cost effectively provide improved convenience and comfort for the practitioner. It will be understood, if desired, that the insert 70 could be color coded. The insert 70 can be molded of any sterilizable plastic such a thermoplastic material commercially available and known as polyphenylsulfone. It will also be understood that a plurality of snap-fit fingers, such as the fingers 72b, can be molded in housing 72a for purposes of releasibly attaching the adaptor to the handpiece 12a.

Figure 10C:
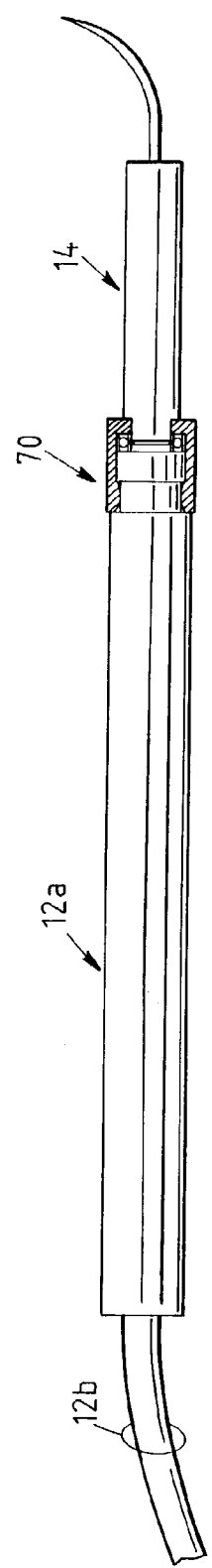
FIG. 10C is an over-all view of an insert as in FIG. 1 combined with an adaptor as in FIG. 10A.

FIG. 10C is an over-all view of insert 14 coupled to handpiece 12a via adaptor 70.

Figure 11A:
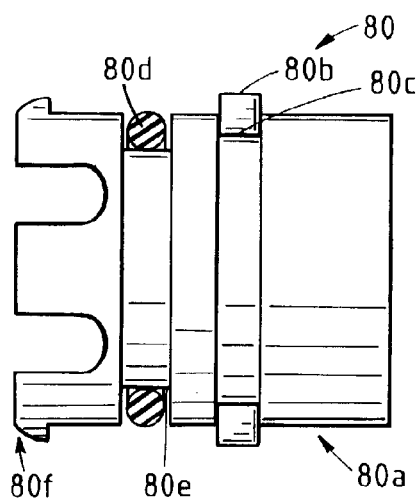
FIG. 11A is an enlarged side view of an alternate embodiment of an insert in accordance with the present invention.
Figure 11B:
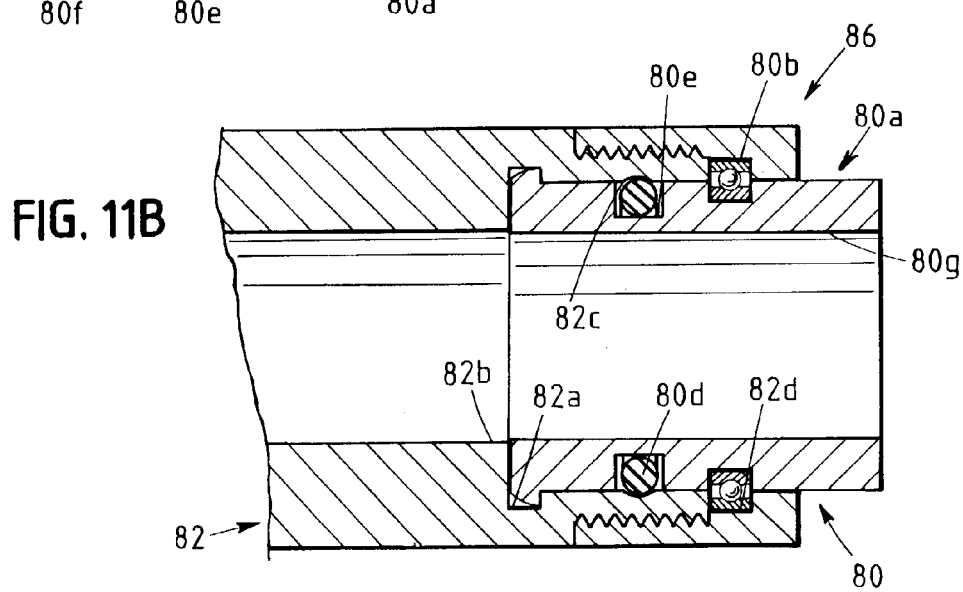
FIG. 11B is an enlarged partial side sectional view of the insert of FIG. 11A inserted into a handpiece of an ultrasonic scaling unit, generally of a type illustrated in FIG. 1.
Figure 11C:
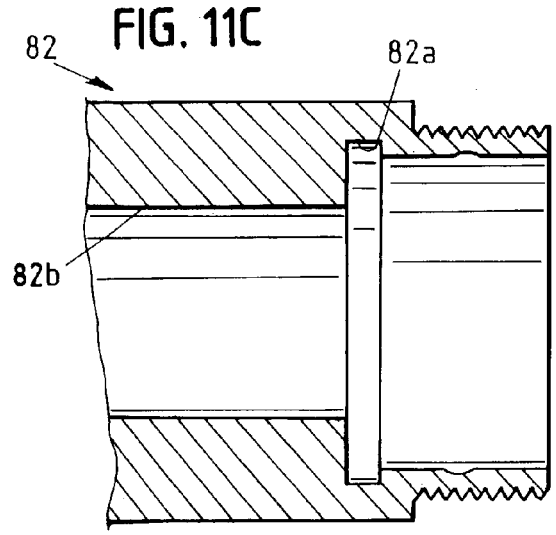
FIG. 11C is a side view of a portion of the handpiece of FIG. 11B.
Figure 11D:
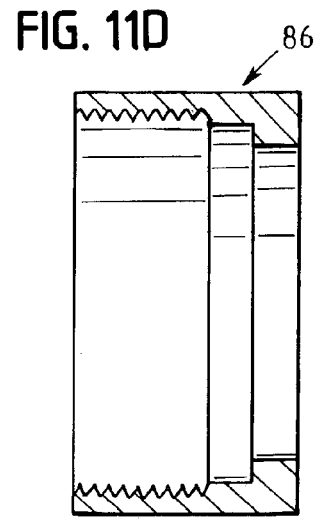
FIG. 11D is a side view of a collar threadable onto the handpiece of FIG. 11B.

FIGS. 11A and 11B illustrate an alternate form of an adaptor 80 usable with a handpiece 82. The adaptor 80 includes a cylindrical body section 80a which carries a bearing 80b which could be implemented as a plastic ring bearing. The bearing 80b is carried in a cylindrical slot 80c in housing 80a.

Housing 80a also carries an O-ring seal 80d in a second slot 80e. Finally, the body 80a terminates at a plurality of deflectable locking fingers 80f. The body 80a is hollow and defines an internal peripheral cylindrical surface 80g.

Insert 80 is slidably receivable into handpiece 82 with a snap-fit. The exterior surfaces of the fingers 80f slidably engage a locking slot 82a formed in an interior peripheral surface 82b of the handpiece 82. The interior peripheral surface 82b also includes a slot 82c for receipt of the O-ring seal 80e, and, a slot 82d which receives the rotary bearing 80b carried by the insert 80. It will be understood that the O-ring 80d provides a fluid seal between handpiece 82 and an insert, such as the insert 14 shown in part in phantom, which has been slidably inserted into the adaptor 80 in contact with the internal peripheral cylindrical surface 80g. When so-inserted, the insert 14 can be rotated, along with adaptor 80 relative to the handpiece 82 so as to promote the convenience and comfort of a practitioner. A collar 86 is threadable onto the end of the handpiece 82 to trap the adaptor 80 in place and prevent axial movement thereof.

Figure 12A:
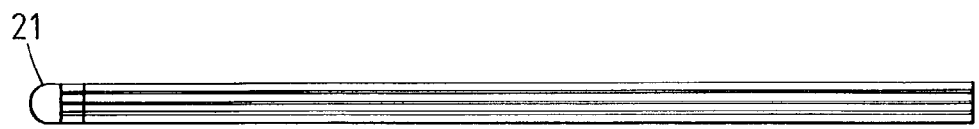
FIGS. 12A, B are top and side views of a preferred form of an ultrasonic transducer.
Figure 12B:
FIG. 12C is an end view of the transducer of FIG. 12B.
Figure 12C:
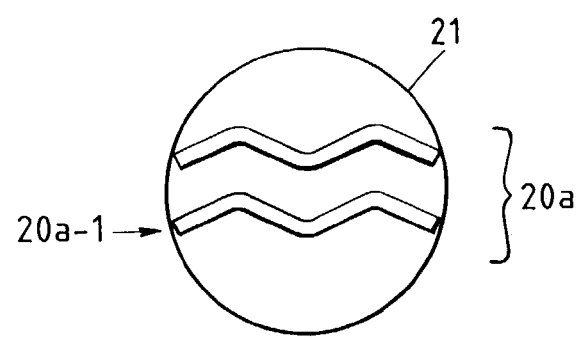

FIGS. 12A–C illustrate details of a preferred structure of stack 20a. By impressing a "W" bend 20a-1 along the length of each member of the stack, as illustrated, stiffness of the stack can be increased. This in turn promotes continued alignment of the stack relative to central axis HP-A, see FIG. 2B, while the insert 20 is being rotated. The improved alignment minimizes the likelihood of the stack 20a rubbing against internal peripheral surface 12d during rotation, hence eliminating a possible source of friction and noise.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. An ultrasonic dental instrument grippable by an operator comprising:
    a handpiece; and
    an ultrasonic insert having two parts, a treatment applying tip is fixedly attached to one part, the one part carrying an ultrasonic transducer, a second part of the insert is rotatable relative to the one part, wherein the insert is removably carried by the handpiece, and, wherein the tip, the one part and the transducer are rotatable together relative to the second part and the handpiece by a force applied only to the one part of the insert.

2. An instrument as in claim 1 wherein the insert is releasibly coupled for axial insertion into and removal from the handpiece.

3. An instrument as in claim 1 wherein the insert carries a user gripping member for rotating the tip.

4. An instrument as in claim 1 wherein the tip is rotatable through an arc on the order of at least two hundred seventy degrees.

5. An instrument as in claim 1 which includes an elastomeric handle wherein the elastomeric handle comprises silicone.

6. An ultrasonic dental instrument grippable by an operator comprising:
    a handpiece; and
    a two part ultrasonic insert with a treatment applying tip fixedly attached to one part, a second part of the insert is rotatable relative to the first part, wherein the insert is removably carried by the handpiece, and, wherein the tip and the one part are rotatable relative to the second part and the handpiece by a force applied only to the one part of the insert, wherein the insert is releasibly coupled for axial insertion into and removal from the handpiece and wherein the insert carries a user comfortable, deformable, elastomeric member whereby the user can rotate the tip relative to the handpiece.

7. An instrument as in claim 6 wherein the tip is rotatable through an arc on the order of at least two hundred seventy degrees.

8. An instrument as in claim 6 wherein the elastomeric member comprises silicone.

9. An ultrasonic dental instrument grippable by an operator comprising:
    a handpiece; and
    an ultrasonic insert with a treatment applying tip wherein the insert is carried by the handpiece, and, wherein the tip is rotatable relative to the handpiece by a force applied only to a portion of the insert, the insert is releasibly coupled for axial insertion into and removal from the handpiece, the insert carries a user comfortable, deformable elastomeric member whereby the user can rotate the tip relative to the handpiece; and wherein the insert includes an elongated body with an end coupled to the tip and a torque transferring cylinder coupled between a portion of body and the elastomeric member whereby the cylinder is mechanically locked to the body such that a rotary force applied to the elastomeric member establishes a torque for rotating the body.

10. An instrument as in claim 9 wherein the cylinder is coupled to the body at a region of minimal axial ultrasonic vibration.

11. An instrument as in claim 9 which includes a cylindrical bearing which is slidably locked to the handpiece in which the torque transferring cylinder rotates.

12. An ultrasonic dental instrument grippable by an operator comprising:
    a handpiece; and
    an ultrasonic insert with a treatment applying tip wherein the insert is carried by the handpiece, and, wherein the tip is rotatable relative to the handpiece by a force applied only to a portion of the insert, wherein the insert is releasibly coupled for axial insertion into and removal from the handpiece, wherein the insert carries a user comfortable, deformable elastomeric member whereby the user can rotate the tip relative to the handpiece; and which includes a rotary bearing positioned adjacent to the elastomeric member whereby the tip and the elastomeric member are rotatably decoupled from and are rotatable together relative to the handpiece.

13. An instrument as in claim 12 wherein the bearing is located at least in part, adjacent to a region of minimal axial ultrasonic vibration.

14. An ultrasonic dental instrument grippable by an operator comprising:
    a handpiece; and
    an ultrasonic insert having two parts, a treatment applying tip is fixedly to one part, the one part carrying an ultrasonic transducer, a second part of the insert is rotatable relative to the one part, wherein the insert is removably carried by the handpiece, and, wherein the tip, the one part and the transducer are rotatable together relative to the second part and the handpiece by a force applied only to the one part of the insert wherein the one part of the insert includes an elongated body with an end coupled to the tip and a torque transferring cylinder coupled between a portion of the body and a cylindrical housing whereby the cylinder is mechanically locked to the body such that a rotary force applied to the cylindrical housing establishes a torque for rotating the body.

15. An instrument as in claim 14 wherein the cylinder is coupled to the body at a region of minimal axial ultrasonic vibration.

16. An instrument as in claim 14 which includes an external annular positioning flange on the body which flange abuts an end of the handpiece when the body is inserted therein.

17. An ultrasonic dental instrument grippable by an operator comprising:
a handpiece; and
an ultrasonic insert with a treatment applying tip wherein the insert is carried by the handpiece, and, wherein the tip is rotatable relative to the handpiece by a force applied only to a portion of the insert, the insert includes an elongated body with an end coupled to the tip and a torque transferring cylinder coupled between a portion of the body and a cylindrical housing whereby the cylinder is mechanically locked to the body such that a rotary force applied to the cylindrical housing establishes a torque for rotating the body, and, which includes a cylindrical bearing which is slidably locked to the handpiece in which the torque transferring cylinder rotates.

18. An ultrasonic dental instrument grippable by an operator comprising:
a handpiece; and
an ultrasonic insert with a treatment applying tip wherein the insert is carried by the handpiece, and, wherein the tip is rotatable relative to the handpiece by a force applied only to a portion of the insert, and, which includes a rotary bearing positioned adjacent to an elastomeric member whereby the tip and the elastomeric member are rotatable together relative to the handpiece.

19. An instrument as in claim 18 wherein the bearing has an end located adjacent to a region of minimal axial ultrasonic vibration of the insert.

20. An ultrasonic dental instrument grippable by an operator comprising:
a handpiece; and
an ultrasonic insert with a treatment applying tip wherein the insert is carried by the handpiece, and, wherein the tip is rotatable relative to the handpiece by a force applied only to a portion of the insert, and, which includes:
a hollow, generally cylindrical bearing member rotatably latched to the insert wherein the cylindrical bearing member slidably engages the handpiece.

21. An instrument as in claim 20 which includes a deformable gripping handle locked to the insert.

22. An instrument as in claim 21 wherein the gripping handle is carried by an element which slidably engages a region of the insert exhibiting minimal vibration.

23. An instrument as in claim 22 wherein the element has first and second sections wherein one section lockingly engages a slot in the minimal vibration region of the body.

24. An instrument as in claim 23 wherein the second section engages the first section with an interference fit.

25. An instrument as in claim 24 wherein the second section has a cylindrical external periphery and carries the deformable gripping handle thereon.

26. An instrument as in claim 24 which includes a conical section which couples to the second section at an end thereof extending toward the tip.

27. An instrument as in claim 20 wherein the insert defines a slot thereon and wherein the cylindrical bearing member is located adjacent to the slot.

28. An instrument as in claim 27 which carries a cylindrical user handle, deformable at least in part, wherein an end of the handle is adjacent to an end of the cylindrical bearing member.

29. An instrument as in claim 27 wherein the slot is located on the insert at a region of minimal axial ultrasonic vibration.

30. An instrument as in claim 29 which carries a cylindrical user handle wherein a portion of the handle lockingly engages the slot and wherein the bearing member is thereby blocked from axial movement relative to the insert.

31. An instrument as in claim 30 wherein a portion of the handpiece slidably engages the bearing member.

32. An ultrasonic dental instrument grippable by an operator comprising:
an ultrasonic insert with a treatment applying tip, a grip, an elongated body, and a transducer, wherein the grip is engaged with the body at a point of minimal vibration and a rotatable sleeve is carried on the body adjacent to the grip.

33. An instrument as in claim 32 wherein the insert is carried by an energizing handpiece.

34. An instrument as in claim 32 wherein the tip is rotatable relative to the handpiece by a force applied to only a portion of the insert.

* * * * *